United States Patent [19]

Flagg

[11] 4,200,749
[45] Apr. 29, 1980

[54] PREPARATION OF HALOGENATED MODIFIED ISOCYANURATES

[75] Inventor: Edward E. Flagg, Midland, Mich.

[73] Assignee: The Dow Chemical Company, Midland, Mich.

[21] Appl. No.: 10,297

[22] Filed: Feb. 8, 1979

[51] Int. Cl.² .......................................... C07D 251/34
[52] U.S. Cl. .................................................. 544/221
[58] Field of Search .......................................... 544/221

[56] References Cited

U.S. PATENT DOCUMENTS

| | | | |
|---|---|---|---|
| 2,947,736 | 8/1960 | Lundberg | 544/221 |
| 3,259,626 | 7/1966 | Muller et al. | 544/193 |
| 3,328,398 | 6/1967 | Cousserans | 544/222 |
| 3,331,839 | 7/1967 | Little | 544/221 |
| 3,470,228 | 9/1969 | Heinert | 544/221 |
| 3,480,627 | 11/1969 | Heinert | 544/221 |
| 3,624,252 | 11/1971 | Labarge | 544/121 |

FOREIGN PATENT DOCUMENTS

| | | | |
|---|---|---|---|
| 1159461 | 12/1963 | Fed. Rep. of Germany | 544/221 |
| 1022670 | 3/1966 | United Kingdom | 544/221 |
| 381668 | 8/1973 | U.S.S.R. | 544/221 |

*Primary Examiner*—John M. Ford
*Attorney, Agent, or Firm*—Douglas N. Deline

[57] ABSTRACT

Halogenated modified isocyanurates of the general formula:

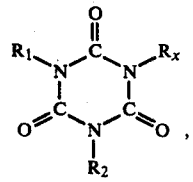

wherein $R_x$ is a halogenated alkyl or alkenyl radical; $R_1$ and $R_2$ are individually either halogenated alkyl radicals, halogenated alkenyl radicals, or unreactive alkyl or aryl moieties, are formed by the reaction of olefins or halogenated olefins with appropriate halogenated modified isocyanate compounds of the general formula:

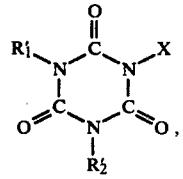

wherein X is a halogen and $R_1'$ and $R_2'$ are individually either halogens or unreactive alkyl or aryl moieties, in the presence of a solvent.

14 Claims, No Drawings

PREPARATION OF HALOGENATED MODIFIED ISOCYANURATES

BACKGROUND OF THE INVENTION

This invention comprises a novel process for the production of halogenated alkyl or alkenyl isocyanurates. Halogenated alkyl isocyanurates have generally been prepared by addition of halogen to isocyanurates containing unsaturated substituents or by nucleophilic substitution of previously prepared alkyl isocyanurates. A third method, disclosed by Müller et al. in U.S. Pat. No. 3,259,626 is the trimerization of a halosubstituted isocyanate according to the formula:

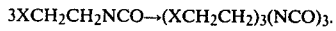

$$3XCH_2CH_2NCO \rightarrow (XCH_2CH_2)_3(NCO)_3.$$

These known processes are limited to production of halogenated alkyl isocyanurates. No known convenient process exists for preparing both halogenated alkyl isocyanurates and halogenated alkenyl isocyanurates.

SUMMARY OF THE INVENTION

This invention is the process for the production of halogenated modified isocyanurates of the general formula

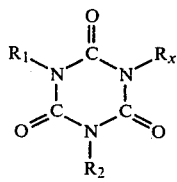

wherein $R_x$ is a halogenated alkyl or alkenyl radical; $R_1$ and $R_2$ are individually either halogenated alkyl radicals, halogenated alkenyl radicals or unreactive alkyl or aryl radicals by the reaction of olefins or halogenated olefins with compounds of the general formula

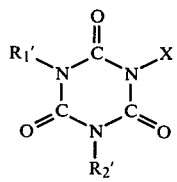

wherein X is a halogen and $R_1'$ and $R_2'$ are individually halogens or unreactive alkyl or aryl moieties. These compounds are useful as fungicides and fire-retardant additives, as disclosed by LaBarge in U.S. Pat. No. 3,624,252.

DETAILED DESCRIPTION OF THE INVENTION

Alkenes, alkadienes, cyclic alkenes and other olefins including halogenated olefins may be used as one reactant in this process. Included are compounds such as ethylene, propene, 1-butene, 2-butene, 1-pentene, 2-pentene, 3-pentene, 1,3-butadiene, cyclohexene, halo and dihalo ethylene, halogenated 1,3-butadiene, etc. By halogen and halo wherever the terms are used is meant fluorine, chlorine, bromine or iodine, however, bromine and chlorine are the preferred halogens and chlorine is the particularly preferred halogen. While virtually any such olefin may be used, higher temperatures and pressures are required for certain olefins, for example, olefins that are highly deactivated by halogen substitution or substituted with groups so as to render the compound sterically hindered. In the preferred embodiment of this invention the olefin reactant is an α-alkene, alkadiene with one double bond in the α position, or cyclic alkene.

The second reactant is a halogenated isocyanurate of the general formula

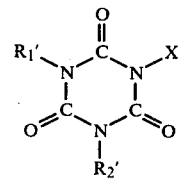

wherein X, $R_1'$ and $R_2'$ are as hereinbefore defined. For example the second reactant may be trihalo isocyanurate, N-benzyl dihalo isocyanurate, N,N-dimethyl halo isocyanurate, etc. The preferred second reactant in this invention is trichloro isocyanurate.

A solvent is employed that may be an excess of the olefinic reactant used in the reaction. Common unsubstituted aliphatic solvents are generally not suitable for use with this invention. The preferred solvent is one in which the halogenated isocyanurate is at least partially soluble. Representative of a preferred solvent is chlorobenzene or other unreactive halogenated aromatic solvent.

The reaction is carried out in any reaction vessel suitably designed to contain the reactants and products under the conditions of the reaction. In the preferred embodiment, elevated temperatures or pressures are not required. Normally temperatures from about 0° C. to about 132° C. are sufficient but higher or lower temperatures may be used depending on the olefin and solvent used. Reaction may occur upon contacting of the two reactants. If less reactive reactants are utilized the reactants may be heated and mixed at an elevated temperature until reaction is substantially complete. If more reactive reactants are utilized the reaction may be slowed by cooling the reaction mixture and/or combining the reactants slowly over an extended time period. For gaseous olefinic reactants a diluent gas, e.g., nitrogen may be mixed with the olefin to limit the rate of reaction.

The mole ratio range of olefinic reactant to trihalo isocyanurate reactant may be varied from as low as about 3 to 1 to large excesses of olefinic reactant, e.g., about 12 to 1. Lower ratios of olefinic reactant, i.e., less than 3 to 1 may also be suitable when the trihalo isocyanurate reactant does not completely dissolve in the solvent used. Optimum ratios of reactants will vary with the choice of reactants and solvents. Such optimum ratio of reactants may easily be determined according to the methods of normal chemical practice.

Recrystallization and purification of the resulting product is accomplished by well-known laboratory methods. A variety of common solvents are suitable for the recrystallization procedure. Good results may be obtained by dissolving the chlorinated isocyanurate product in a mixture containing methanol, diethyl ether and hexane. Activated charcoal is also used in the purification step according to well-known techniques in the art. The purified products are generally soluble in nonpolar and aromatic solvents. Yields approach stoichiometric quantities based on the amount of halogenated isocyanurate reactant used. Unreacted excess olefinic reactant may of course be recovered and reused.

The invention allows greater control of the stoichiometry of resulting chlorinated isocyanurate products than is possible with presently known methods. For example, when mono halogenated isocyanurate reactant is used the product will contain only one halogenated alkyl or alkenyl group. Similarly when dihalo isocyanurate reactant is employed the product will consist of predominately di(halo alkyl or alkenyl)isocyanurate. In addition the amount of halogen substitution in the resulting product may be easily controlled in the invention by use of unhalogenated or differing halogenated olefins respectively as one reactant. For example, use of unhalogenated alkenes with the double bond occurring between the first and second carbon atoms as one reactant and trihalo isocyanurate as the other reactant will produce almost entirely tri($\beta$-halo alkyl)isocyanurate. Similarly use of halogenated olefins with one double bond occurring between the first and second carbon atom will produce halogenated alkyl or alkenyl isocyanurates containing one halogen at the $\beta$ position and other halogens in positions corresponding to their initial position in the olefin reactant. It may easily be seen that a wide variety of halogenated alkyl or alkenyl isocyanurates may be produced by means of this invention. Furthermore the invention provides a means to definitively control the degree of halogenation and location of the halogen in the resulting product. The invention also provides a means to produce one particular halogenated alkyl or alkenyl isocyanurate in preference to other halogenated alkyl or alkenyl isocyanurates without requiring as one step the separation of a mixture containing several halogenated alkyl or alkenyl isocyanurates.

SPECIFIC EMBODIMENTS OF THE INVENTION

Example 1: Preparation of Tri-(2-chlorocyclohexyl)isocyanurate

Trichloroisocyanurate (11.62 g technical grade) was added to chlorobenzene (approximately 80 g) in a 500 ml flask equipped with a condenser, mechanical stirrer, and dropping funnel. In a separate container, 18.60 g of cyclohexene was added to approximately 30.3 g of chlorobenzene. Upon addition at ambient temperature of approximately one-fourth of the cyclohexene solution to the mixture of trichloroisocyanurate in chlorobenzene an exothermic reaction was observed. To limit the rate of reaction the remaining cyclohexene solution was transferred to the dropping funnel, the flask was cooled to about 0° C.–1° C. and the cyclohexene solution was added dropwise with stirring. After addition of the cyclohexene the flask and contents were heated to the reflux temperature and maintained at that temperature for several hours. After refluxing, the solution was cooled and placed on a still for solvent removal. After removal of the solvent a gummy solid remained which upon purification by recrystallization gave a colorless solid. Chemical analysis by common oxidation techniques gave the following results for components besides oxygen:

| Tri-(2-chlorocyclohexyl)isocyanurate | % C | % H | % Cl | % N |
| --- | --- | --- | --- | --- |
| calculated | 52.7 | 6.3 | 22.2 | 8.8 |
| found | 49.4 | 5.9 | 19.2 | 10.9 |

Analysis by infrared absorption spectroscopy showed olefin addition had occurred.

Example 2: Preparation of Tri-(2-chloroethyl)isocyanurate

Trichloro isocyanurate (20.7 g) was mixed with 500 ml of hexane contained in a three-necked flask equipped with a mechanical stirrer, dip tube, and an exit condenser with a nitrogen bubbler. The mixture was cooled to 0° C.–1° C. and an ethylene-nitrogen gas mixture was added. No reaction was noted. The ethylene-nitrogen gas mixture was continued at ambient temperature for approximately 3 to 4 hours. A white solid was present undissolved in the hexane solution. Analysis by infrared spectroscopy indicated the solid consisted of primarily unreacted trichloro isocyanurate. The hexane was removed from the flask and freshly distilled chlorobenzene added to the remaining white, dry solid. Stirring was begun with concurrent heating. The ethylene-nitrogen gas mixture was once more added. A mild exothermic reaction was observed and the solid slowly dissolved. Ethylene-nitrogen gas mixture addition continued for approximately one hour after all solid had dissolved. Heating was stopped and the solvent removed by distillation leaving a colorless solid. Subsequent chemical analysis by common oxidation techniques gave the following results for components besides oxygen:

| Tri-(2-chloroethyl)isocyanurate | % C | % H | % Cl | % N |
| --- | --- | --- | --- | --- |
| calculated | 34.1 | 3.8 | 33.6 | 13.3 |
| found | 34.6 | 3.8 | 27.8 | 15.8 |

Infrared spectrographic analysis indicated olefinic addition had occurred.

Example 3: Preparation of Tri-(2-chloro-3-butenyl)isocyanurate

Trichloro isocyanurate (23 g) was added to 500 ml of chlorobenzene placed in a 1 liter, three-necked flask previously flushed with dry nitrogen, and equipped with a mechanical stirrer, dip tube, and an exit condenser. Excess 1,3-butadiene was added by being bubbled through this mixture at ambient temperature over a time period of approximately 2 or 3 hours. An exothermic reaction was observed upon initial addition of the 1,3-butadiene. After completion of 1,3-butadiene addition a small amount of unreacted trichloro isocyanurate remained. The reaction mixture was heated to the boiling point and the remaining solids removed by filtration. Removal of solvent by distillation left a viscous liquid having the following analysis:

| Tri-(2-chloro-3-butenyl)isocyanurate | % C | % H | % N | % Cl |
| --- | --- | --- | --- | --- |
| calculated | 45.6 | 4.6 | 10.7 | 26.9 |
| found | 44.9 | 4.4 | 10.7 | 27.0 |

Analysis by infrared spectrometry showed olefin addition had occurred.

Example 4: Preparation of Addition Product of Trichloroisocyanurate and Dicyclopentadiene Chlorobenzene solvent was dried by contacting with phosphorus pentoxide and then filtered. Solid trichloroisocyanurate (15.8 g) was added to a liter flask equipped with a dropping funnel, stirrer and thermometer containing about 250 ml of the dried and filtered chlorobenzene.

Commercially obtained dicyclopentadiene (95 percent purity), was also dried by contacting with phosphorus pentoxide and filtered. An excess amount, approximately 52 ml, having a density of 0.93 g/cc, was added to the dropping funnel containing approximately 100 ml of dried and filtered chlorobenzene. The mixture was added slowly with stirring over approximately 1 hour to the trichloroisocyanurate mixture at ambient temperature.

An exothermic reaction was observed on addition of the dicyclopentadiene mixture and the solid trichloroisocyanurate dissolved slowly over the course of dicyclopentadiene addition. A maximum temperature of 57° C.–58° C. was noted during the course of dicyclopentadiene addition.

The reaction mixture was heated to approximately 100° C. and maintained at that temperature with stirring for approximately 16 hours. During the course of the heating the solution changed color from an initial pale yellow to dark green ultimately leaving a clear green solution.

After cooling, the solution was filtered leaving no observable precipitate and the solvent removed under a vacuum. Approximately 35 g of a dark green solid was isolated. The solid was found to be soluble in methylene chloride and chlorobenzene but insoluble in diethyl ether, ethanol and hexane. Recrystallization from methylene chloride/hexane solution produced a light green solid.

Incipient decomposition of the product was observed to begin at approximately 152° C. Analysis by infrared spectroscopy indicated olefin addition had occurred.

Example 5: Preparation of Addition Product of Trichloroisocyanurate and 2,5-cyclohexadiene-1,4-dione Repeating the reaction conditions of Example 3 using as a diene excess 2,5-cyclohexadiene-1,4-dione added from a dropping funnel results in an exothermic reaction and production of 1,3,5-tris(6-chloro-2,5-dioxo-3-cyclo-hexen-1-yl)-s-triazine-2,4,6(1H,3H,5H)trione along with mono- and disubstituted reaction products.

I claim:

1. A process for the production of halogenated isocyanurate compounds of the formula:

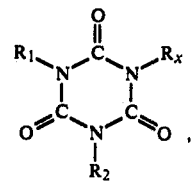

wherein $R_x$ is a halogenated alkyl or alkenyl radical; $R_1$ and $R_2$ are individually either halogenated alkyl radicals, halogenated alkenyl radicals or unreactive alkyl or aryl moieties, said process comprising reacting an olefin with a second reactant compound of the general formula:

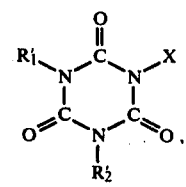

wherein X is halogen; and $R_1'$ and $R_2'$ are individually halogens or unreactive alkyl or aryl moieties in the presence of a halogenated aromatic solvent or an aliphatic solvent wherein the said second reactant compound is at least partially soluble.

2. The process of claim 1 wherein the second reactant compound contains a single nitrogen bonded halogen.

3. The process of claim 2 wherein the halogen is chlorine.

4. The process of claim 1 wherein the second reactant compound contains two nitrogen bonded halogens.

5. The process of claim 4 wherein the halogens are chlorine.

6. The process of claim 1 wherein the second reactant compound contains three nitrogen bonded halogens.

7. The process of claim 6 wherein the second reactant compound is trichloro isocyanurate.

8. The process of claim 7 wherein the olefin reactant is cyclohexene.

9. The process of claim 7 wherein the olefin reactant is ethylene.

10. The process of claim 7 wherein the olefin reactant is 1,3-butadiene.

11. The process of claim 1 wherein the mole ratio of olefin reactant to second reactant compound is at least about 3:1.

12. The process of claim 1 wherein the solvent is an excess of olefinic reactant.

13. The process of claim 1 wherein the solvent is chlorobenzene.

14. The process of claim 1 wherein the reaction takes place at a temperature from about 0° C. to about 132° C. and at a pressure of about atmospheric pressure.

* * * * *